US00PP19617P2

(12) United States Plant Patent
Dümmen

(10) Patent No.: US PP19,617 P2
(45) Date of Patent: Jan. 6, 2009

(54) ***OSTEOSPERMUM* PLANT NAMED 'DUETIPICHAR'**

(50) Latin Name: *Osteospermum ecklonis*
Varietal Denomination: Duetipichar

(75) Inventor: Tobias Dümmen, Rheinberg (DE)

(73) Assignee: Capitol Green Investments Ltd., Grand Cayman (KY)

( * ) Notice: Subject to any disclaimer, the term of this patent is extended or adjusted under 35 U.S.C. 154(b) by 58 days.

(21) Appl. No.: 11/807,346

(22) Filed: May 26, 2007

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent L Bell
(74) *Attorney, Agent, or Firm*—C. A. Whealy

(57) ABSTRACT

A new and distinct cultivar of *Osteospermum* plant named 'Duetipichar', characterized by its compact, upright and mounded plant habit; freely branching growth habit; freely flowering habit; and daisy-type inflorescences with elongated oblong-shaped ray florets that are purple and light pink in color.

1 Drawing Sheet

Botanical designation: *Osteospermum ecklonis.*
Cultivar denomination: 'Duetipichar'.

BACKGROUND OF THE INVENTION

The present invention relates to a new and distinct cultivar of *Osteospermum* plant, botanically known as *Osteospermum ecklonis,* and hereinafter referred to by the name 'Duetipichar'.

The new *Osteospermum* is a product of a planned breeding program conducted by the Inventor in Rheinberg, Germany. The objective of the program is to create and develop new *Osteospermum* cultivars with uniformly mounded plant habit, freely flowering habit and attractive inflorescence coloration.

The new *Osteospermum* originated from an open-pollination by the Inventor in August, 2003 of a proprietary selection of *Osteospermum ecklonis* identified as code number Q02-93-15, not patented, as the female, or seed, parent with an unknown selection of *Osteospermum ecklonis* as the male, or pollen, parent. The new *Osteospermum* was discovered and selected by the Inventor as a single flowering plant within the progeny of the stated open-pollination in a controlled environment in Rheinberg, Germany in May, 2004.

Asexual reproduction of the new *Osteospermum* by terminal cuttings in a controlled environment in Rheinberg, Germany since July, 2004, has shown that the unique features of this new *Osteospermum* are stable and reproduced true to type in successive generations.

SUMMARY OF THE INVENTION

The cultivar Duetipichar has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Duetipichar'. These characteristics in combination distinguish 'Duetipichar' as a new and distinct cultivar of *Osteospermum:*

1. Compact, upright and mounded plant habit.
2. Freely branching growth habit.
3. Freely flowering habit.
4. Daisy-type inflorescences with elongated oblong-shaped ray florets that are purple and light pink in color.

In side-by-side comparisons conducted in Rheinberg, Germany, plants of the new *Osteospermum* differ from plants of the female parent selection in the following characteristics:

1. Plants of the new *Osteospermum* are more vigorous than plants of the female parent selection.
2. Plants of the new *Osteospermum* are more freely branching than plants of the female parent selection.
3. Plants of the new *Osteospermum* and the female parent selection differ in ray floret coloration.

Plants of the new *Osteospermum* can be compared to plants of the *Osteospermum* cultivar Duesumpink, disclosed in U.S. Plant Pat. No. 15,938. In side-by-side comparisons conducted in Rheinberg, Germany, plants of the new *Osteospermum* differed from plants of the cultivar Duesumpink in the following characteristics:

1. Plants of the new *Osteospermum* were more vigorous than plants of the cultivar Duesumpink.
2. Plants of the new *Osteospermum* had broader leaves and shorter leaf petioles than plants of the cultivar Duesumpink.
3. Plants of the new *Osteospermum* had larger inflorescences than plants of the cultivar Duesumpink.
4. Plants of the new *Osteospermum* and the cultivar Duesumpink differed in ray floret color as plants of the cultivar Duesumpink had lighter-colored ray florets.

BRIEF DESCRIPTION OF THE PHOTOGRAPH

The accompanying photograph illustrates the overall appearance of the new *Osteospermum.* This photograph shows the colors as true as it is reasonably possible to obtain in colored reproductions of this type. Colors in the photograph may differ slightly from the color values cited in the detailed botanical description which accurately describe the colors of the new *Osteospermum*. The photograph comprises a side perspective view of a typical flowering plant of 'Duetipichar'.

DETAILED BOTANICAL DESCRIPTION

In the following description, color references are made to The Royal Horticultural Society Colour Chart, 1995 Edition, except where general terms of ordinary dictionary significance are used. The aforementioned photograph, following observations and measurements describe plants grown in Rheinberg, Germany during the spring in a glass-covered greenhouse and under conditions and practices which approximate those generally used in commercial *Osteospermum* production. During the production of the plants, day and night temperatures averaged 18° C. and light levels averaged 4,500 lux. Measurements and numerical values represent averages for typical flowering plants. Plants were about 16 weeks old when the photograph and description were taken.

Botanical classification: *Osteospermum ecklonis* cultivar Duetipichar.

Parentage:

*Female, or seed, parent.*—Proprietary selection of *Osteospermum ecklonis* identified as code number Q02-93-15, not patented.

*Male, or pollen, parent.*—Unknown selection of *Osteospermum ecklonis,* not patented.

Propagation:

*Type.*—Terminal vegetative cuttings.

*Time to initiate roots.*—About ten days at 20° C.

*Time to produce a rooted cutting.*—About three weeks at 20° C.

*Root description.*—Fine, fibrous; white in color.

*Rooting habit.*—Freely branching.

Plant description:

*Plant form/growth habit.*—Compact, upright and mounded plant habit. Inflorescences positioned well above the foliar plane. Moderately vigorous growth habit.

*Plant height.*—About 15 cm.

*Plant diameter.*—About 14 cm.

*Lateral branches.*—Quantity per plant: Freely branching, about seven lateral branches per plant. Length: About 14 cm. Diameter: About 5 mm. Internode length: About 8.3 mm. Strength: Strong. Texture: Smooth, glabrous. Color: 144B.

*Foliage description.*—Arrangement: Alternate, simple. Length: About 5.3 cm. Width: About 2.8 cm. Shape: Spatulate. Apex: Acute. Base: Attenuate. Margin: Dentate. Texture, upper surface: Pubescent; leathery. Texture, lower surface: Smooth, glabrous; leathery. Venation pattern: Pinnate. Color: Developing foliage, upper surface: 137B. Developing foliage, lower surface: 144A. Fully expanded foliage, upper surface: 137A; venation, 144B. Fully expanded foliage, lower surface: 137B to 137C; venation, 144B. Petiole length: About 2.8 cm. Petiole diameter: About 3.25 mm. Petiole texture, upper and lower surfaces: Smooth, glabrous. Petiole color, upper surface: 144B. Petiole color, lower surface: 144A.

Inflorescence description:

*Appearance.*—Daisy-type inflorescence form with elongated oblong-shaped ray florets. Inflorescences positioned above the foliage, arising from leaf axils. Disc and ray florets developing acropetally on a capitulum. Inflorescences face mostly upright to outward. Freely flowering habit; about 45 inflorescences develop over time per plant. Inflorescences persistent. Inflorescences not fragrant.

*Flowering response.*—In Rheinberg, Germany, plants of the new *Osteospermum* flower continuously from spring to autumn. Early flowering habit, plants begin flowering about six weeks after planting. Inflorescences last about three days on the plant.

*Inflorescence bud.*—Height: About 1.8 cm. Diameter: About 1 cm. Shape: Ovate. Color: 137B tinted with 154A.

*Inflorescence size.*—Diameter: About 6.4 cm. Depth (height): About 2.2 cm. Disc diameter: About 1.2 cm. Receptacle diameter: About 4 mm. Receptacle height: About 3 mm.

*Ray florets.*—Shape: Elongated oblong. Length: About 3.3 cm. Width: About 9 mm. Apex: Emarginate. Base: Obtuse. Margin: Entire. Texture: Smooth, glabrous. Number of ray florets per inflorescence: About 21 in about two whorls. Color: When opening, upper surface: Towards the margin, 78A to 78B; towards the base, 69D. When opening, lower surface: 91A and 78C. Fully opened, upper surface: Towards the margin, 78B; towards the base, 69D. Fully opened, lower surface: 91A and 78C.

*Disc florets.*—Shape: Tubular; apex dentate, five-pointed. Length: About 5 mm. Diameter, apex: About 2 mm. Diameter, base: About 1 mm. Number of disc florets per inflorescence: About 50. Color: Immature: 93C. Mature: Apex: 93A. Mid-section: 154D. Base: 154B.

*Phyllaries.*—Quantity per inflorescence: About 18. Length: About 1.1 cm. Width: About 2 mm. Shape: Lanceolate. Apex: Apiculate. Base: Acute. Margin: Entire. Texture, upper and lower surfaces: Smooth, glabrous; leathery. Color, upper surface: 137B to 137C. Color, lower surface: 137C.

*Peduncles.*—Length: About 4.8 cm. Diameter: About 2 mm. Strength: Strong. Aspect: Mostly upright. Texture: Leathery. Color: 144A.

*Reproductive organs.*—Androecium: Present on disc florets only. Anther shape: Ovate. Anther length: About 2 mm. Anther color: 98A. Pollen amount: Abundant. Pollen color: 17A. Gynoecium: Present on both ray and disc florets. Pistil length: About 7 mm. Stigma shape: Lanceolate. Stigma color: 79A. Style length: About 3 mm. Style color: 79A. Ovary color: 144C.

*Seeds.*—Length: About 7 mm. Diameter: About 3 mm. Color: 199A.

Disease/pest resistance: Plants of the new *Osteospermum* have not been shown to be resistant to pathogens and pests common to *Osteospermums.*

Temperature tolerance: Plants of the new *Osteospermum* have been observed to tolerate temperatures ranging from about 5° C. to about 35° C.

It is claimed:

1. A new and distinct *Osteospermum* plant named 'Duetipichar' as illustrated and described.

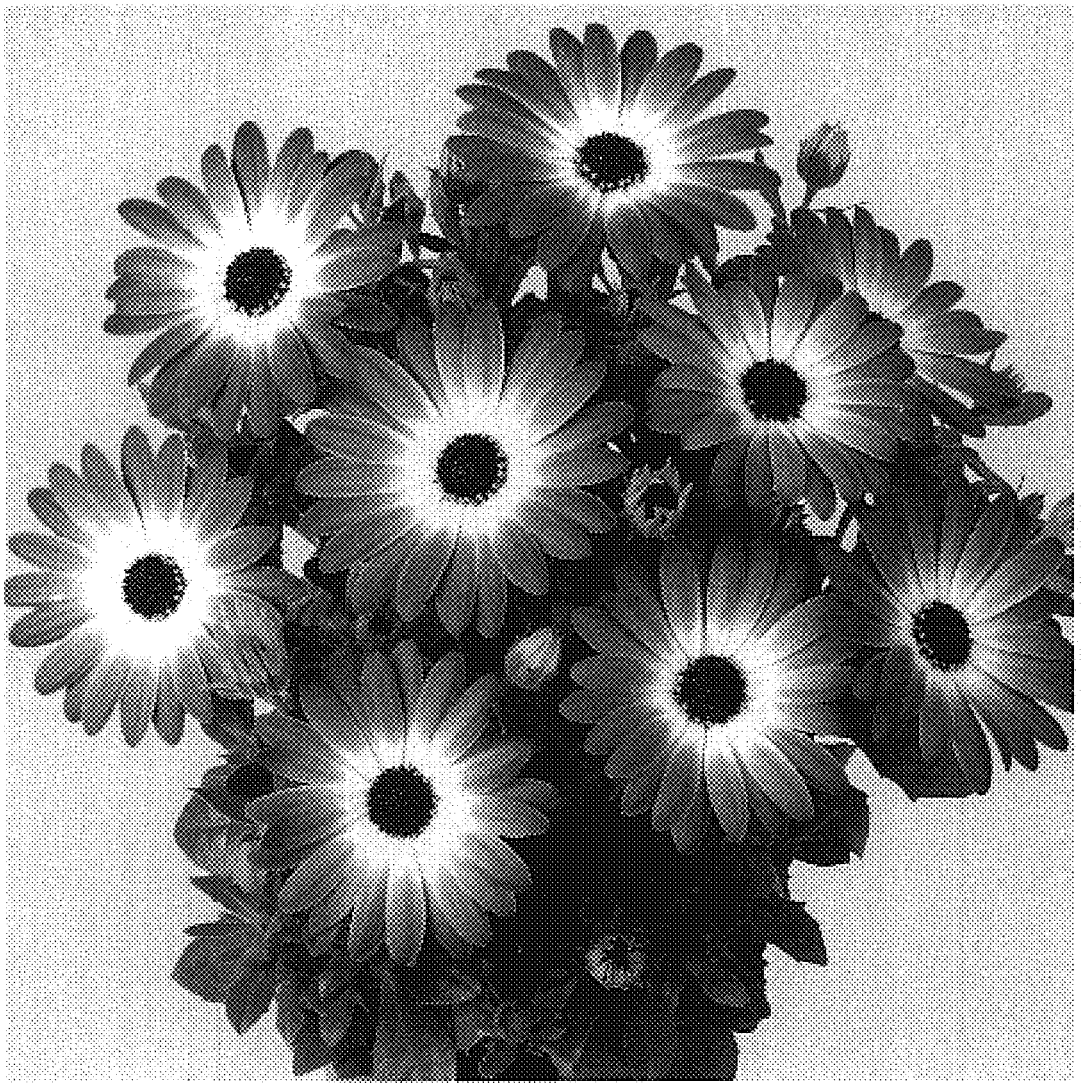

* * * * *